(12) United States Patent
Teshima et al.

(10) Patent No.: US 9,040,227 B2
(45) Date of Patent: May 26, 2015

(54) MICROSTRUCTURE MANUFACTURING METHOD

(75) Inventors: Takayuki Teshima, Yokohama (JP); Yutaka Setomoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 181 days.

(21) Appl. No.: 13/399,651

(22) Filed: Feb. 17, 2012

(65) Prior Publication Data

US 2012/0219916 A1 Aug. 30, 2012

(30) Foreign Application Priority Data

Feb. 24, 2011 (JP) ................. 2011-038559

(51) Int. Cl.
| | | |
|---|---|---|
| *G03F 1/58* | (2012.01) | |
| *C25D 5/12* | (2006.01) | |
| *G02B 5/18* | (2006.01) | |

(52) U.S. Cl.
CPC ... *C25D 5/12* (2013.01); *G02B 5/18* (2013.01)

(58) Field of Classification Search
CPC ............................ H01L 21/0271; G03F 1/146
USPC .................................................. 430/315, 318
See application file for complete search history.

(56) References Cited

U.S. PATENT DOCUMENTS

| | | | |
|---|---|---|---|
| 2005/0260522 A1* | 11/2005 | Weber et al. | 430/270.1 |
| 2010/0270165 A1* | 10/2010 | Cohen et al. | 205/118 |

FOREIGN PATENT DOCUMENTS

| | | |
|---|---|---|
| JP | 2007-010713 A | 1/2007 |
| JP | 2009-169098 A | 7/2009 |

* cited by examiner

*Primary Examiner* — Daborah Chacko Davis
(74) *Attorney, Agent, or Firm* — Canon U.S.A. Inc., IP Division

(57) ABSTRACT

A microstructure manufacturing method includes forming a layer of a photosensitive resin on a substrate surface having an electrical conductivity, forming a structure of the photosensitive resin by exposing the layer of the photosensitive resin to light and developing the layer of the photosensitive resin to expose a part of the substrate surface, forming a first plated layer on the exposed part of the substrate surface by soaking the structure of the photosensitive resin in a first plating solution, curing the structure of the photosensitive resin after forming the first plated layer, removing at least part of the first plated layer after curing the structure of the photosensitive resin, and forming a second plated layer on a part where the first plated layer is removed, by soaking the structure of the photosensitive resin in a second plating solution different from the first plating solution.

11 Claims, 6 Drawing Sheets

MICROSTRUCTURE MANUFACTURING METHOD

BACKGROUND OF THE INVENTION

1. Field of the Invention

The present invention relates to a method for manufacturing a microstructure.

2. Description of the Related Art

A microstructure having a periodic structure is used in several devices as a grating. A microstructure made of gold which absorbs X-rays is used in a nondestructive inspection for industrial use or an X-ray examination for medical use. The nondestructive inspection or the X-ray examination utilizes the X-ray absorption contrast method to obtain an image of an object or a living body. However, it is difficult to obtain an image of a soft material or a soft tissue using these techniques because the soft material or the soft tissue absorbs only a little X-ray.

The phase contrast method, which utilizes a phase difference of X-rays, has been studied at synchrotron radiation facilities since the 1990s. The phase contrast method using an X-ray tube instead of the synchrotron (e.g. propagation-based method, Talbot interferometer method) has also been studied.

The X-ray Talbot interferometer generally uses a microstructure as an absorption grating. It is preferable that the absorption grating is made by plating a periodic structure with metal (e.g. gold). But, as a pitch of the periodic structure becomes narrower and an aspect ratio of the periodic structure becomes higher, sticking of the periodic structure occurs in more places. The aspect ratio is the ratio (h/w) of the height (depth) h to width w of the periodic structure.

When the periodic structure having many sticking places is filled with the plated metal, the absorption grating may have shifts of the pitch. So, it is difficult to obtain a desirable phase image when the X-ray Talbot interferometer uses the absorption grating having many shifts of the pitch.

SUMMARY OF THE INVENTION

Aspects of the present invention are directed to a microstructure manufacturing method enabling manufacturing of a metal microstructure having little shifts of the pitch.

According to an aspect of the present invention, a microstructure manufacturing method includes forming a layer of a photosensitive resin on a substrate surface having an electrical conductivity, forming a structure of the photosensitive resin by exposing the layer of the photosensitive resin to light and developing the layer of the photosensitive resin to expose a part of the substrate surface, forming a first plated layer on the exposed part of the substrate surface by soaking the structure of the photosensitive resin in a first plating solution, curing the structure of the photosensitive resin after forming the first plated layer, removing at least part of the first plated layer after curing the structure of the photosensitive resin, and forming a second plated layer on a part where the first plated layer is removed, by soaking the structure of the photosensitive resin in a second plating solution different from the first plating solution.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

FIGS. 1A to 1G illustrate an exemplary embodiment of the microstructure manufacturing method according to the present invention.

Figure 1A:
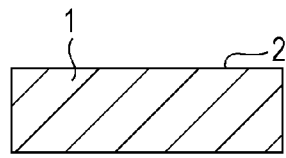
FIGS. 1A to 1G illustrate a microstructure manufacturing method according to an exemplary embodiment of the present invention.

A first step of "forming a photosensitive resin layer 3 on a substrate surface 2 having electrical conductivity" will be described below based on FIGS. 1A and 1B.

The substrate surface 2 has electrical conductivity. Metal, semiconductor, or insulator can be used as the material of the substrate 1. In the case that metal is used as the material of the substrate 1, there is no need to form an electrically conductive layer on the substrate 1. In the case that semiconductor is used as the material of the substrate 1, there is no need to form an electrically conductive layer on the substrate 1 as long as the semiconductor has enough electrical conductivity to be plated. In the case that a surface of the substrate 1 does not have enough electrical conductivity, an electrically conductive layer is formed on the substrate 1. The electrically conductive layer can be formed by a thin-film formation method such as a vacuum evaporation method, a spin coat method, or a dip method. According to one aspect of the invention, the substrate surface 2 can consist essentially of gold.

Figure 1B:
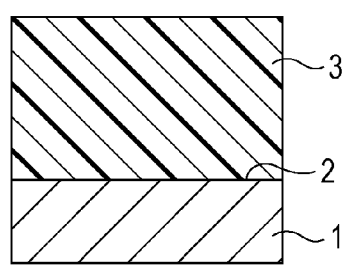

As illustrated in FIG. 1B, a photosensitive resin layer 3 is formed on the substrate surface 2. The photosensitive resin layer 3 can be formed by applying the photosensitive resin in liquid form to the substrate surface 2. In this case, a spin coat method or a dip method can be utilized. Also, the photosensitive resin layer 3 can be formed by applying the photosensitive resin in film form to the substrate surface 2. In the present exemplary embodiment, a photosensitive resin which can be cured (hardened) by light and can be further cured (hardened) by heat can be used as the photosensitive resin of the photosensitive resin layer 3. In particular, negative resist of SU-8 (manufactured by KAYAKU Micro Chemical Co., Ltd), KMPR (manufactured by KAYAKU Micro Chemical Co., Ltd), or the like can be used as the photosensitive resin of the photosensitive resin layer 3.

Figure 1C:
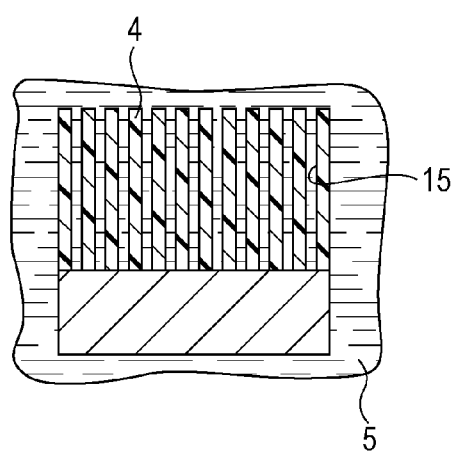

Next, a second step of "forming a photosensitive resin structure 4 by exposing the photosensitive resin layer 3 to light and developing the photosensitive resin layer 3 to expose a part of the substrate surface" will be described below based on FIG. 1C.

The photosensitive resin layer 3 is exposed to light using an exposure apparatus, and a part of the photosensitive resin layer 3 is cured with the light. Then, the cured photosensitive resin layer 3 is developed by developer to form concave portions 15. The photosensitive resin layer 3 includes through-holes and the substrate surface 2 is exposed at the bottom of the concave portions 15.

Ultraviolet light, synchrotron radiation light (X-ray), or electron beam can be used as the exposure light. The exposure light is determined by the aspect ratio of the concave portion 15 and characteristics and the film thickness of the photosensitive resin. In the case that the height of the photosensitive resin structure 4 is high and the pitch of it is narrow, the synchrotron radiation light may be used as the exposure light. In the present exemplary embodiment, it is preferred that the aspect ratio (height (depth) h/width w) of the concave portion 15 is 5 or more, and it is further preferred that the aspect ratio is 12 or more and 100 or less.

The photosensitive resin structure 4 is rinsed with rinse liquid 5 to remove the developer liquid, and this prevents overdevelopment. The rinse liquid 5 is selected based on the photosensitive resin used. Water is preferably used as the rinse liquid 5. If a first plating solution used in the third step will not be contaminated and a first plated layer will be formed, it is not required to use water as rinse liquid 5. For example, isopropyl alcohol may be used as the rinse liquid 5 other than water.

Figure 1D:
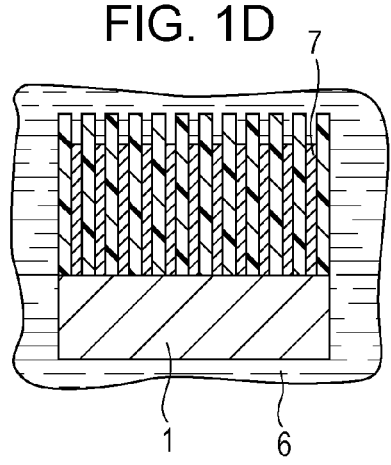

A third step of "forming a first plated layer on the exposed part of the substrate surface 2 by soaking the photosensitive resin structure 4 in a first plating solution 6" will be described below based on FIG. 1D.

In the third step, the photosensitive resin structure 4 which has been rinsed with rinse liquid 5 is soaked in the first plating solution 6, and the first plated layer 7 is formed on the exposed part of the substrate surface 2 (on the bottom of the concave portion 15). In the present exemplary embodiment, the photosensitive resin structure 4 is soaked in liquids and is not dried, during the time from when the photosensitive resin layer 3 is developed in the second step until the first plated layer 7 is formed in the third step. This can prevent the occurrence of a surface tension in the concave portion 15, which is caused when the photosensitive resin structure 4 is dried. So, the walls of the concave portion 15 will not stick to each other by the surface tension. In this specification, "dry" means "blow off" or "vaporize" the residual liquid.

As the first plating solution 6, a solution which has a low attacking property to the photosensitive resin structure 4 may be selected. The first plated layer 7 may consist essentially of nickel, copper, iron, tin or alloy of them. These metals can be etched by a wide variety of etchants. It is preferable that the first plated layer 7 has enough thickness to prevent walls of the concave portion 15 from sticking to each other when the photosensitive resin is cured in the next step. The first plated layer 7 may be formed by electro plating, electroless plating, or a combination of them.

Figure 1E:
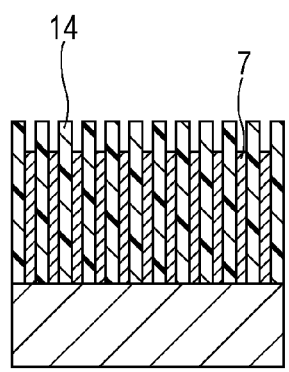

Next, a fourth step of "curing the photosensitive resin structure 4" will be described below based on FIG. 1E.

In the fourth step, the photosensitive resin structure 4 is cured after forming the first plated layer 7, and the cured photosensitive resin structure 4 is obtained. The resin curing method is determined according to a property of the photosensitive resin. In the case that the photosensitive resin is an ultraviolet curing resin, the photosensitive resin structure 4 is cured by irradiating the ultraviolet light. In the case that the photosensitive resin is a thermosetting resin, the photosensitive resin structure 4 is cured by heating. The etching resistance of the photosensitive resin structure 4 becomes higher by curing the photosensitive resin structure 4. And the cured photosensitive resin structure 4 has etching resistance against the first plating solution and a second plating solution used in the next step. In the fourth step, it is preferable that the photosensitive resin is a thermosetting resin and the photosensitive resin structure 4 is cured by heating.

The photosensitive resin which is exposed to light in the second step has etching resistance against the first plating solution, and the photosensitive resin which is exposed to light in the fourth step has etching resistance against the second plating solution. In the second step, the photosensitive resin is cured (exposed to light) so that the photosensitive resin structure 4 will have a predetermined shape. By this amount of curing, the exposed photosensitive resin has etching resistance against the first plating solution, but it does not have enough etching resistance against the second plating solution.

The photosensitive resin which is exposed in the second step has a higher etching resistance against the first plating solution than against the second plating solution. The photosensitive resin which is cured in the fourth step has a higher etching resistance against the second plating solution than the photosensitive resin which is exposed in the second step.

In the second step, the photosensitive resin is cured by exposing it to light. The photosensitive resin structure 4 remains on the substrate surface 2 by exposing the photosensitive resin layer 3 to light with a proper exposure dose. It is difficult to form the photosensitive resin structure 4 having a preferable shape, if the exposure dose is not properly set.

On the other hand, in the fourth step, the photosensitive resin is cured so that the etching resistance of it becomes higher. In the fourth step, the photosensitive resin which is cured by exposing to light in the second step is further cured (by heating or exposing to light), so the cured photosensitive resin has etching resistance against the second plating solution.

Next, a fifth step of "removing at least part of the first plated layer 7" will be described below based on FIG. 1F.

In the fifth step, a part of or the whole of the first plated layer 7 is removed from the cured photosensitive resin structure 14 by etchant, and the etchant is removed with cleaning liquid. The etchant has a low attacking property to the cured photosensitive resin structure 14 and the substrate 1. In the present exemplary embodiment, there is no need to remove the whole of the first plated layer 7.

Figure 2A:
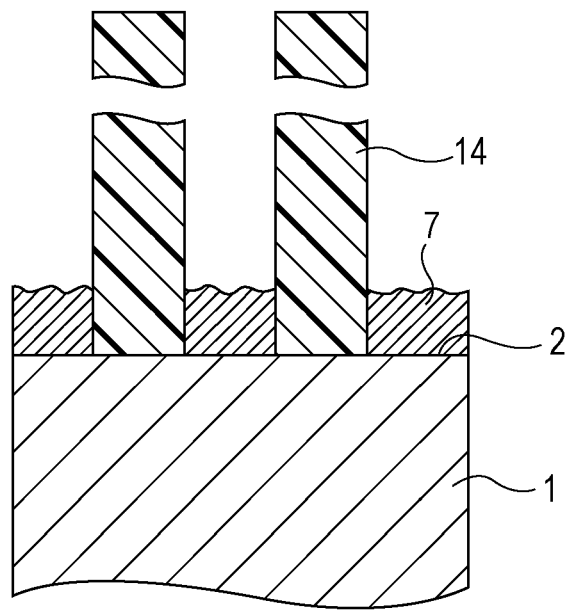
FIGS. 2A to 2B illustrate a fifth step of the microstructure manufacturing method according to the exemplary embodiment.
Figure 2B:
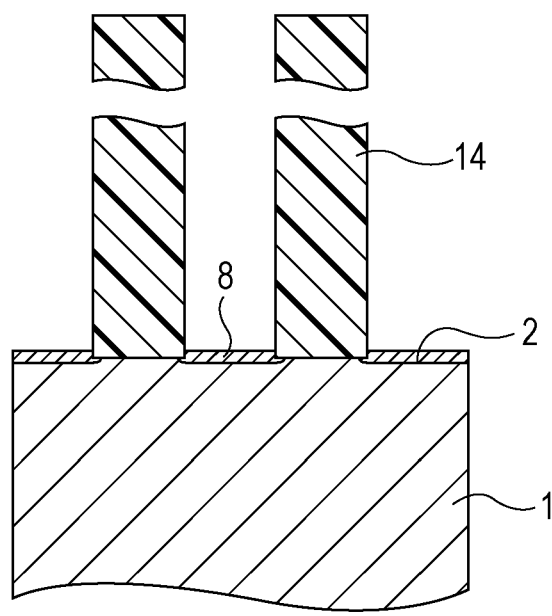

FIGS. 2A and 2B are diagrams for explaining the fifth step of the microstructure manufacturing method. As illustrated in FIG. 2A, the cured photosensitive resin structure 14 can be rigidly held on the substrate surface 2 by remaining a part of the first plated layer 7. In the case that an alloy layer is formed between the substrate surface 2 and the first plated layer 7 as illustrated in FIG. 2B, the alloy layer 8 may not be removed. The cured photosensitive resin structure 14 can be rigidly held on the substrate surface 2 by the alloy layer 8. In the case that the substrate surface 2 includes gold, the alloy layer 8 may be formed at the boundary face between the substrate surface 2 and the first plated layer 7, because gold is easy to alloy. Because etchants which can etch gold are limited, the gold is not removed by etching when the first plated layer 7 is removed by etching.

Figure 1F:
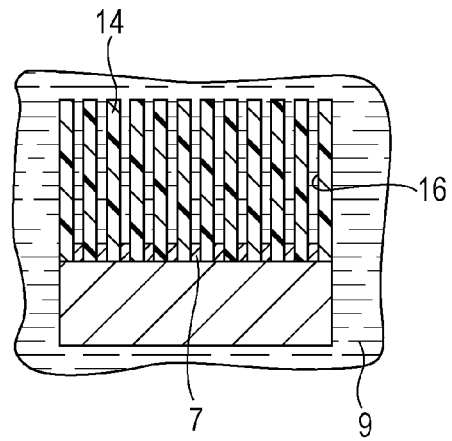

In the present exemplary embodiment, the etchant is removed from the substrate 1 with the cleaning liquid 9 as illustrated in FIG. 1F. Water-soluble solvent is used as the cleaning liquid 9. In particular, water may be used. If a second plating solution used in the next step will not be contaminated and a second plated layer will be formed, it is not required to use water as cleaning liquid 9. For example, isopropyl alcohol may be used as the cleaning liquid 9 instead of water.

Figure 1G:
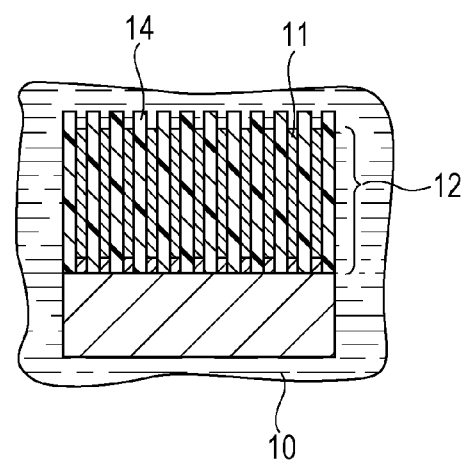

Next, a sixth step of "forming the second plated layer 11 by soaking the cured photosensitive resin structure 14 in a second plating solution 10 different from the first plating solution 6" will be described below based on FIG. 1G.

In the sixth step, the cured photosensitive resin structure 14 which has been cleaned with the cleaning liquid 9 is soaked in the second plating solution 10, and the second plated layer 11 is formed on a part where the first plated layer has been removed in the fifth step. In other words, the second plated layer 11 is formed on the substrate surface 2, the remaining first plated layer 7 (FIG. 2A), or the alloy layer 8 (FIG. 2B). In the case that the whole of the first plated layer 7 is removed to expose a part of the substrate surface 2 in the fifth step, the second plated layer 11 is formed on the exposed part of the substrate surface 2 in the sixth step.

In the present exemplary embodiment, the cured photosensitive resin structure 14 is soaked in liquids and is not dried, during the time from when the first plated layer 7 is etched in the fifth step until the second plated layer 11 is formed in the sixth step. This can prevent the occurrence of a surface tension in the concave portion 16, which is caused when the cured photosensitive resin structure 14 is dried. So, walls of the concave portion 16 do not stick to each other by the surface tension, and the microstructure 12 having little shifts of the pitch can be obtained.

Metal such as gold, platinum, or palladium may be used as the second plated layer 11. The second plated layer 11 may be formed by electro plating, electroless plating, or combination of them.

By using gold as the second plated layer 11, an X-ray absorption grating (microstructure) having narrow pitch and high aspect ratio can be manufactured. X-ray transmission areas of the absorption grating are so small that the absorption grating enables the imaging with high spatial coherence.

The present exemplary embodiment enables the prevention of the walls of the concave portion from sticking to each other due to surface tension. So, the present exemplary embodiments may enable the manufacture of a microstructure having little shifts of the pitch.

In the case that the substrate surface 2 consists essentially of gold, the cured photosensitive resin structure 14 may be firmly fixed on the substrate surface 2 by the alloy layer 8.

In the case that the first plated layer consists essentially of nickel, copper, iron, tin, or alloy of them, the first plated layer 11 may be formed without damaging the photosensitive resin structure 4. These metals can be etched by a wide variety of etchants.

In the case that the second plated layer 11 consists essentially of gold, a microstructure 12 made of highly X-ray absorbent material can be manufactured.

By using the synchrotron radiation light as the exposure light, the photosensitive resin structure 4 having narrow pitch may be formed. This enables to form the microstructure having narrow pitch.

First Example

FIGS. 3A to 3h illustrate a first example according to the microstructure manufacturing method of the present invention.

Figure 3A:
FIGS. 3A to 3H illustrate a microstructure manufacturing method according to a first exemplary example of the present invention.
Figure 3B:
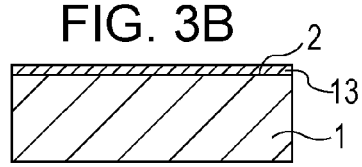

In the present example, a silicon wafer is used as the substrate 1 (FIG. 3A). The wafer is double sided, and its diameter is 4 inches and its thickness is 525 μm. A titanium film with a thickness of 5 nm and a gold film with a thickness of 100 nm are formed sequentially in this order on the substrate 1 as the electrically conductive layer 13 by an electron beam deposition apparatus (FIG. 3B).

Figure 3C:
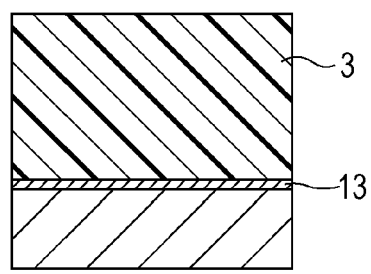
Figure 3D:
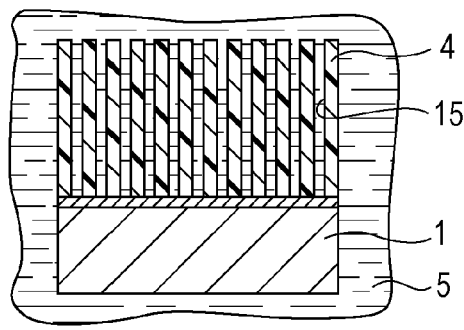

The negative resist of SU-8 (manufactured by KAYAKU Micro Chemical Co., Ltd) is used as the photosensitive resin. The SU-8 is applied on the electrically conductive layer 13, and a photosensitive resin layer 3 with a thickness of 40 μm is formed, the photosensitive resin layer 3 is soft-baked at 95° C. for ten minutes (FIG. 3C). Next, the photosensitive resin layer 3 is exposed to ultraviolet light by MPA600 (manufactured by Canon), and the exposed photosensitive resin layer 3 is baked at 65° C. for five minutes. A latent image is formed in the photosensitive resin layer 3 in such a manner that a square pole pattern 2 μm on a side is two-dimensionally arranged at the 4 μm pitch. The latent image is developed by a developer of the SU-8 (manufactured by KAYAKU Micro Chemical Co., Ltd). A part of the photosensitive resin layer 3 which is not exposed to the ultraviolet light is dissolved in the developer, and the photosensitive resin structure 4 is formed in such a manner that a square pole pattern, 2 μm on a side and 40 μm in height, is two-dimensionally arranged at the 4 μm pitch. After the developing, the photosensitive resin structure 4 is rinsed by isopropyl alcohol, and the developer is removed from the photosensitive resin structure 4 (FIG. 3D), and the photosensitive resin structure 4 is soaked in purified water.

In the present example, nickel sulfamate plating solution is used as the first plating solution 6, and the first plated layer 7 consists essentially of nickel.

Figure 3E:
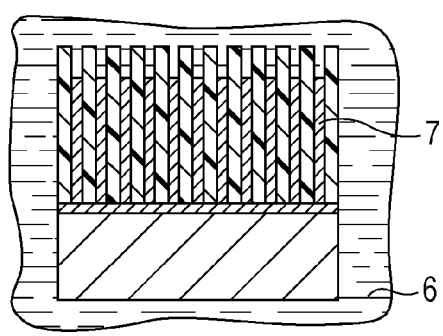

The composition of the nickel sulfamate plating solution is as follows: nickel sulfamate hexahydrate: 450 (g/L), nickel chloride hexahydrate: 5 (g/L), and boric acid: 30 (g/L). The photosensitive resin structure 4 which has been soaked in purified water is further soaked in the nickel sulfamate plating solution without drying the photosensitive structure 4. The plating is carried out by energization through the electrically conductive layer 13 at a current density of 1.5 A/dm$^2$ at room temperature for 2 hours, and the first plated layer 7 made of nickel with a thickness of 36 μm is formed (FIG. 3E). The photosensitive structure 4 is taken out of the nickel sulfamate plating solution, and the photosensitive structure 4 is cleaned by purified water, and the photosensitive structure 4 is dried by blowing nitrogen gas. Since there is the first plated layer 7 in the concave portion 15, the walls of the concave portion 15 do not stick to each other.

Figure 3F:
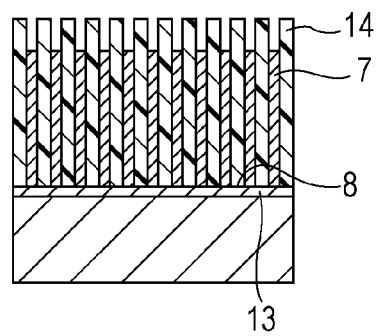
Figure 3G:
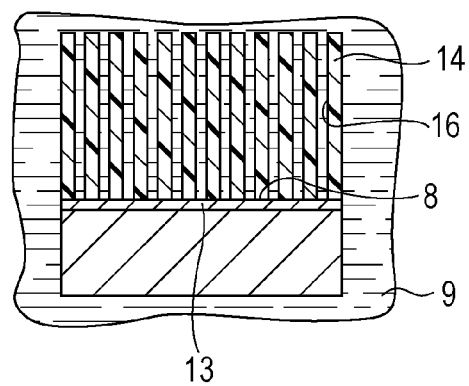

Next, the photosensitive resin structure 4 is cured by heating the substrate 1 at 200° C., and the cured photosensitive resin structure 14 is formed (FIG. 3F). By the curing, the etching resistance of the photosensitive resin structure 4 becomes higher. And an alloy layer 8 is formed between the electrically conductive layer 13 and the first plated layer 7. After that, the concave portion 16 is formed by etching the first plated layer 7 by etchant. The composition of the etchant is as follows: nitric acid: 248 ml, ammonium peroxodisulfate: 132 g, purified water: 750 ml. The first plated layer 7 is etched by the etchant, and the alloy layer 8 remains on the electrically conductive layer 13. After the etching, the photosensitive resin structure 4 is cleaned with purified water as cleaning liquid (FIG. 3G), and the photosensitive resin structure 4 is soaked in the second plating solution 10 without drying the photosensitive resin structure 4.

In the present example, a gold plating solution is used as the second plating solution 10, and the second plated layer 11 consists essentially of gold. The golden plating is carried out with use of a gold plating solution (MICROFAB Au1101: Electroplating Engineers of Japan Ltd.) at 60° C. as the temperature of the gold plating solution at a current density of 0.2

Figure 3H:
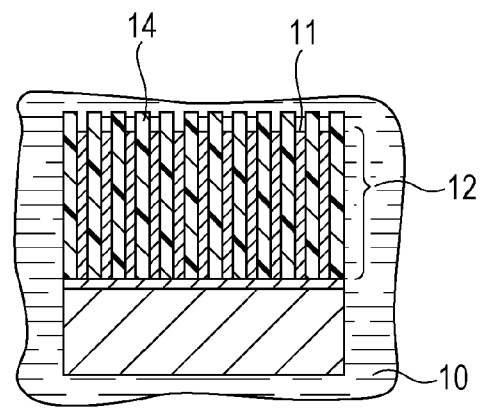

A/dm² for 6 hours. This plating forms the plated layer made of gold with a thickness of 38 μm. The substrate is taken out of the gold plating solution, and the substrate 1 is cleaned by purified water, and the substrate 1 is dried by blowing nitrogen gas. As explained above, a gold microstructure 12 having a mesh shape and a high aspect ratio (2 μm in width and 38 μm in height) is obtained (FIG. 3H).

When the mesh shaped gold microstructure 12 is observed from above by an X-ray microscope, the area of the photosensitive resin transmits the X-ray, but the area of the gold absorbs the X-ray. So, the image contrast of the mesh shaped gold microstructure 12 is high.

First Comparative Example

In the first comparative example, the same process is performed until the photosensitive resin structure has been formed in the second step of the first example. In the first comparative example, the photosensitive resin structure 4 is rinsed by isopropyl alcohol after the developing, and the developer is removed from the photosensitive resin structure 4, and the photosensitive structure 4 is dried by blowing nitrogen gas. The walls of the concave portion 15 stick to each other, because a surface tension of the isopropyl alcohol on the photosensitive structure 4 is caused.

Second Comparative Example

In the second comparative example, the same process is performed until the second step of the first example. In the second comparative example, the photosensitive resin structure 4 which has been soaked in purified water is further soaked in a gold plating solution without drying the photosensitive resin structure 4. The golden plating is carried out with use of the gold plating solution (MICROFAB Au1101: Electroplating Engineers of Japan Ltd.) at 60° C. as the temperature of the gold plating solution at a current density of 0.2 A/dm². The photosensitive resin structure 4 is eroded by the gold plating solution, and a part of the photosensitive resin structure 4 is missing from the electrically conductive layer 13, and gold is deposited on the electrically conductive layer 13 where the part of the photosensitive resin structure 4 had been disposed before the plating.

Second Example

FIGS. 4A to 4H illustrate a second example according to the microstructure manufacturing method of the present invention.

Figure 4A:
FIGS. 4A to 4H illustrate a microstructure manufacturing method according to a second exemplary example of the present invention.
Figure 4B:

In the present example, a silicon wafer is used as the substrate 1 (FIG. 4A). The wafer is double sided, and its diameter is 4 inches and its thickness is 525 μm. A chromium film with a thickness of 5 nm and a platinum film with a thickness of 100 nm are formed sequentially in this order on the substrate 1 as the electrically conductive layer 13 by a vacuum sputtering apparatus (FIG. 4B).

Figure 4C:
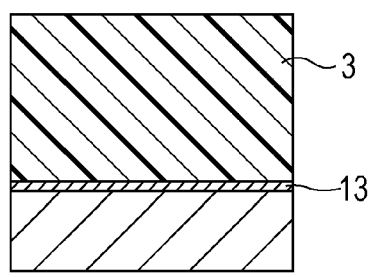
Figure 4D:
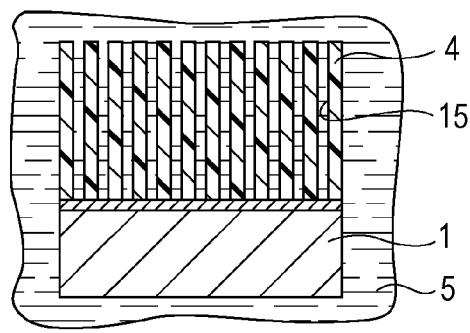

The negative resist of SU-8 (manufactured by KAYAKU Micro Chemical Co., Ltd) is used as the photosensitive resin. The SU-8 is applied on the electrically conductive layer 13, and a photosensitive resin layer 3 with a thickness of 60 μm is formed, the photosensitive resin layer 3 is soft-baked at 95° C. for ten minutes (FIG. 4C). Next, the photosensitive resin layer 3 is exposed to synchrotron radiation light by X-ray exposure apparatus, and the exposed photosensitive resin layer 3 is baked at 65° C. for five minutes. A latent image is formed in the photosensitive resin layer 3 in such a manner that a square pole pattern 2 μm on a side is two-dimensionally arranged at the 4 μm pitch. The latent image is developed by a developer of the SU-8 (manufactured by KAYAKU Micro Chemical Co., Ltd). A part of the photosensitive resin layer 3 which is not exposed to the synchrotron radiation light is dissolved in the developer, and the photosensitive resin structure 4 is formed in such a manner that a square pole pattern, 2 μm on a side and 60 μm in height, is two-dimensionally arranged at the 4 μm pitch. After the developing, the photosensitive resin structure 4 is rinsed by isopropyl alcohol, and the developer is removed from the photosensitive resin structure 4 (FIG. 4D), and the photosensitive resin structure 4 is soaked in purified water.

In the present example, copper sulfate plating solution is used as the first plating solution 6, and the first plated layer 7 consists essentially of copper.

Figure 4E:
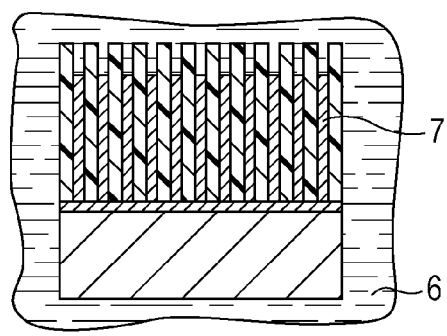

The composition of the copper sulfate plating solution is as follows: copper sulfate pentahydrate: 200 (g/L), 98% concentrated sulfuric acid: 14 (g/L), Cu-Brite VFII-A (manufactured by EBARA-UDYLITE CO., LTD): 1 (g/L), and Cu-Brite VFII-A (manufactured by EBARA-UDYLITE CO., LTD): 1 (g/L). The photosensitive resin structure 4 which has been soaked in purified water is further soaked in the copper sulfate plating solution without drying the photosensitive structure 4. The plating is carried out by energization through the electrically conductive layer 13 at a current density of 1.5 A/dm² at room temperature for 3 hours, and the first plated layer 7 made of copper with a thickness of 56 μm is formed (FIG. 4E). The photosensitive structure 4 is taken out of the copper sulfate plating solution, and the photosensitive structure 4 is cleaned by purified water, and the photosensitive structure 4 is dried by blowing nitrogen gas. Since there is the first plated layer 7 in the concave portion 15, the walls of the concave portion 15 do not stick to each other.

Figure 4F:
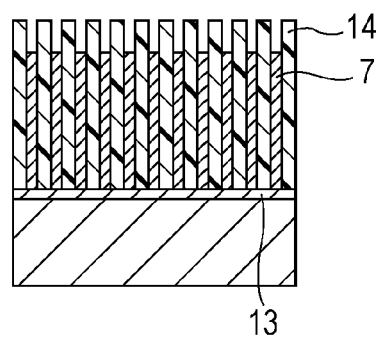
Figure 4G:
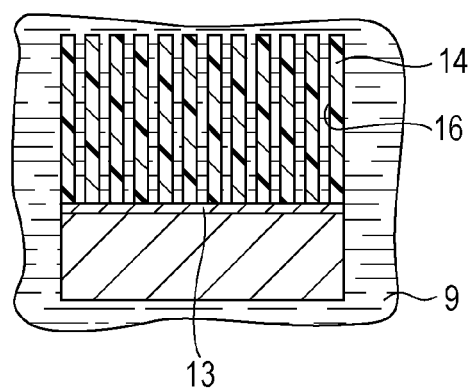

Next, the photosensitive resin structure 4 is cured by heating the substrate 1 at 200° C., and the cured photosensitive resin structure 14 is formed (FIG. 4F). By the curing, the etching resistance of the photosensitive resin structure 4 becomes higher. After that, the concave portion 16 is formed by etching the first plated layer 7 with etchant. The composition of the etchant is as follows: nitric acid: 248 ml, ammonium peroxodisulfate: 132 g, purified water: 750 ml. After the etching, the photosensitive resin structure 4 is cleaned with purified water as cleaning liquid (FIG. 4G), and the photosensitive resin structure 4 is soaked in the second plating solution 10 without drying the photosensitive resin structure 4.

Figure 4H:
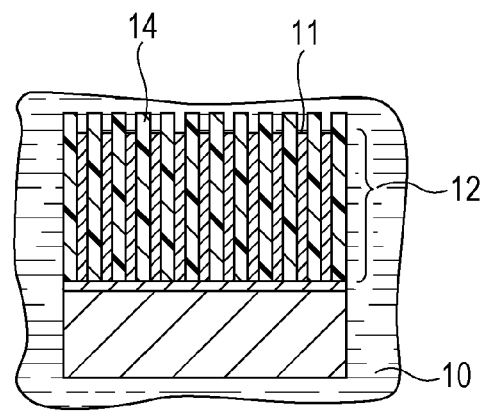

In the present example, gold plating solution is used as the second plating solution 10, and the second plated layer 11 consists essentially of gold. The golden plating is carried out with use of a gold plating solution (MICROFAB Au1101: Electroplating Engineers of Japan Ltd.) at 60° C. as the temperature of the gold plating solution at a current density of 0.2 A/dm² for 8 hours. This plating forms the plated layer made of gold with a thickness of 56 μm. The substrate is taken out of the gold plating solution, and the substrate 1 is cleaned by purified water, and the substrate 1 is dried by blowing nitrogen gas. As explained above, a gold microstructure 12 having a mesh shape and a high aspect ratio (2 μm in width and 56 μm in height) is obtained (FIG. 4H).

When the mesh shaped gold microstructure 12 is observed from above by an X-ray microscope, the area of the photosensitive resin transmits the X-ray, but the area of the gold absorbs the X-ray. So, the image contrast of the mesh shaped gold microstructure 12 is high.

Third Example

FIGS. 5A to 5g illustrate a third example according to the microstructure manufacturing method of the present invention.

Figure 5A:
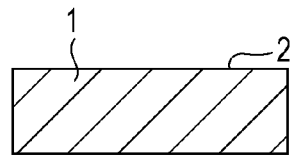
FIGS. 5A to 5G illustrate a microstructure manufacturing method according to a third exemplary example of the present invention.
Figure 5B:
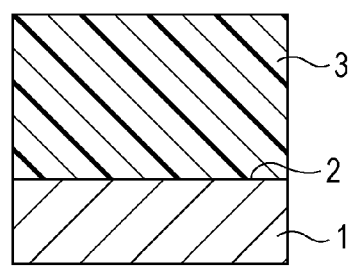
Figure 5C:
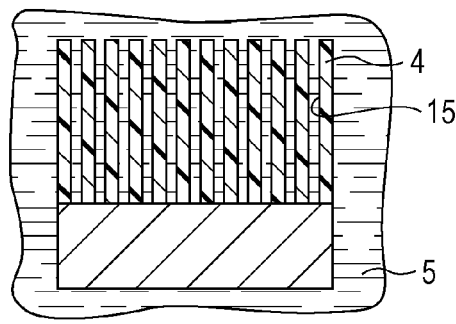

In the present example, a stainless plate is used as the substrate 1 (FIG. 5A). The substrate 1 includes the substrate surface 2 which has electrical conductivity. The negative resist of SU-8 (manufactured by KAYAKU Micro Chemical Co., Ltd) is used as the photosensitive resin. The SU-8 is applied on the stainless plate, and a photosensitive resin layer 3 with a thickness of 60 μm is formed, the photosensitive resin layer 3 is soft-baked at 95° C. for ten minutes (FIG. 5B). Next, the photosensitive resin layer 3 is exposed to synchrotron radiation light by X-ray exposure apparatus, and the exposed photosensitive resin layer 3 is baked at 65° C. for five minutes. A latent image is formed in the photosensitive resin layer 3 in such a manner that a square pole pattern 2 μm on a side is two-dimensionally arranged at the 4 μm pitch. The latent image is developed by a developer of the SU-8 (manufactured by KAYAKU Micro Chemical Co., Ltd). A part of the photosensitive resin layer 3 which is not exposed to the synchrotron radiation light is dissolved in the developer, and the photosensitive resin structure 4 is formed in such a manner that a square pole pattern, 2 μm on a side and 60 μm in height, is two-dimensionally arranged at the 4 μm pitch. After the developing, the photosensitive resin structure 4 is rinsed by isopropyl alcohol, and the developer is removed from the photosensitive resin structure 4 (FIG. 5C), and the photosensitive resin structure 4 is soaked in purified water.

Figure 5D:
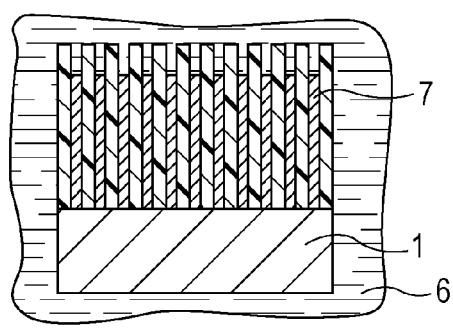

In the present example, nickel sulfamate plating solution is used as the first plating solution 6, and the first plated layer 7 consists essentially of nickel (FIG. 5D).

The composition of the nickel sulfamate plating solution is as follows: nickel sulfamate hexahydrate: 450 (g/L), nickel chloride hexahydrate: 5 (g/L), and boric acid: 30 (g/L). The photosensitive resin structure 4 which has been soaked in purified water is further soaked in the nickel sulfamate plating solution without drying the photosensitive structure 4. The plating is carried out by energization through the stainless plate at a current density of $1.5 A/dm^2$ at room temperature for 3 hours, and the first plated layer 7 made of nickel with a thickness of 55 μm is formed. The photosensitive structure 4 is taken out of the nickel sulfamate plating solution, and the photosensitive structure 4 is cleaned by purified water, and the photosensitive structure 4 is dried by blowing nitrogen gas. Since there is the first plated layer 7 in the concave portion 15, the walls of the concave portion 15 do not stick to each other.

Figure 5E:
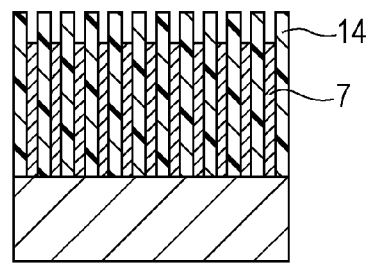
Figure 5F:
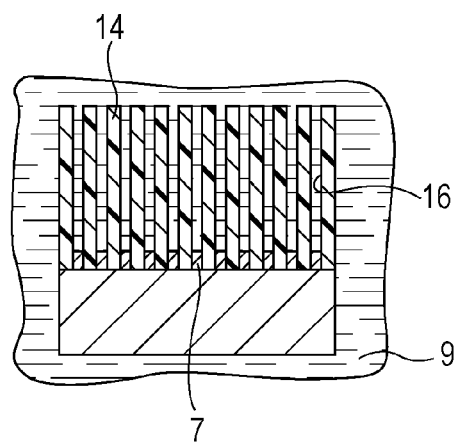

Next, the photosensitive resin structure 4 is cured by heating the substrate 1 at 200° C., and the cured photosensitive resin structure 14 is formed (FIG. 5E). By the curing, the etching resistance of the photosensitive resin structure 4 becomes higher. After that, the concave portion 16 is formed by etching the first plated layer 7 by etchant. The composition of the etchant is as follows: nitric acid: 248 ml, ammonium peroxodisulfate: 132 g, purified water: 750 ml. The first plated layer 7 is etched approximately 50 μm in the thickness direction of the first plated layer 7. So, the etching is stopped when the first plated layer on the stainless plate becomes approximately 5 μm. The photosensitive resin structure 4 is cleaned with purified water (FIG. 5F), and the photosensitive resin structure 4 is soaked in the second plating solution 10 without drying the photosensitive resin structure 4.

Figure 5G:
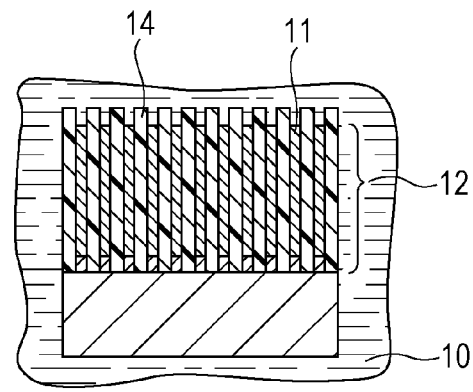

In the present example, gold plating solution is used as the second plating solution 10, and the second plated layer 11 consists essentially of gold. The golden plating is carried out with use of a gold plating solution (MICROFAB Au1101: Electroplating Engineers of Japan Ltd.) at 60° C. as the temperature of the gold plating solution at a current density of 0.2 $A/dm^2$ for 7 hours. This plating forms the plated layer made of gold with a thickness of 50 μm on the remaining first plated layer 7 made of nickel with a thickness of 5 μm. The substrate 1 is taken out of the gold plating solution, and the substrate 1 is cleaned by purified water, and the substrate 1 is dried by blowing nitrogen gas. As explained above, a gold microstructure 12 having a mesh shape and a high aspect ratio (2 μm in width and 50 μm in height) is obtained (FIG. 5G).

When the mesh shaped gold microstructure 12 is observed from above by an X-ray microscope, the area of the photosensitive resin transmits the X-ray, but the area of the gold absorbs the X-ray. So, the image contrast of the mesh shaped gold microstructure 12 is high.

The microstructure according to the present invention can be used for an X-ray absorption grating, an X-ray beam splitter, a photonic crystal, or a metal mesh of a transmission electron microscope.

Figure 6:
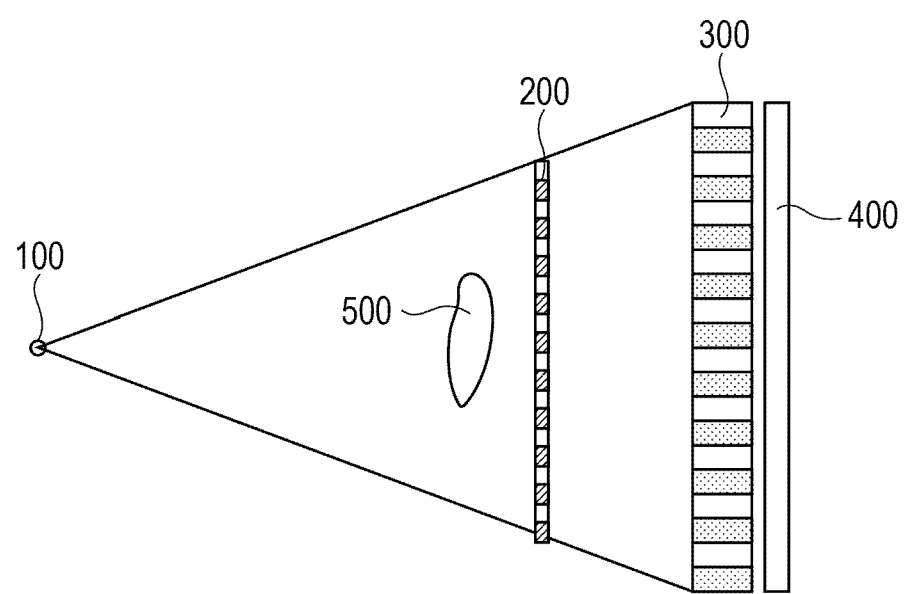
FIG. 6 illustrates a structure of an imaging apparatus according to an exemplary embodiment of the present invention.

In the following, an imaging apparatus utilizing the X-ray Talbot interference method will be described with reference to FIG. 6. FIG. 6 illustrates a configuration of an imaging apparatus using the microstructure manufactured in the above-described exemplary embodiment or examples as an X-ray absorption grating.

The imaging apparatus according to the present exemplary embodiments includes an X-ray source 100 for emitting spatially coherent X-ray, a diffraction grating 200 for periodically modulating the phase of the X-ray, an absorption grating 300 in which an X-ray absorption portion (shield portion) and a transmission portion are arranged, and a detector 400 for detecting the X-ray. The absorption grating 300 is the microstructure manufactured by the above-described exemplary embodiments or examples.

When a subject 500 is positioned between the X-ray source 100 and the diffraction grating 200, information about X-ray phase shift due to the subject 500 is detected as moiré by the detector. In other words, this imaging apparatus obtains an image of the subject 500 by imaging moiré which holds phase information of the subject 500. Execution of phase retrieval processing such as Fourier transform based on this detection result enables a phase image of the subject to be obtained.

Since the imaging apparatus according to the present exemplary embodiment uses an absorption grating having little shifts of the pitch, it can obtain a phase image of a subject more accurately.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-038559, filed Feb. 24 2011, which is hereby incorporated by reference herein in its entirety.

What is claimed is:

1. A microstructure manufacturing method comprising:
   forming a layer of a photosensitive resin on a substrate surface having an electrical conductivity;
   exposing a pattern on the layer of the photosensitive resin to light;
   developing the layer of the photosensitive resin to form a structure of the photosensitive resin that exposes a part of the substrate surface;
   forming a first plated layer on the exposed part of the substrate surface by soaking the structure of the photosensitive resin in a first plating solution;
   curing the structure of the photosensitive resin by at least one of exposing the structure to light and heating the structure, after forming the first plated layer;
   removing at least part of the first plated layer after curing the structure of the photosensitive resin; and forming a second plated layer on a part where the first plated layer is removed, by soaking the structure of the photosensitive resin in a second plating solution different from the first plating solution, wherein the second plated layer and any remaining part of the first plated layer form the microstructure, wherein the photosensitive resin is a negative photosensitive resin, and wherein the aspect ratio of a concave portion of the microstructure is 12 or more and 100 or less.

2. The microstructure manufacturing method according to claim 1, wherein the exposed photosensitive resin has an etching resistance against the first plating solution, and wherein the cured photosensitive resin has an etching resistance against the second plating solution.

3. The microstructure manufacturing method according to claim 1, wherein an etching resistance of the exposed photosensitive resin against the first plating solution is higher than an etching resistance of the exposed photosensitive resin against the second plating solution, and wherein the cured photosensitive resin has a higher etching resistance against the second plating solution than the exposed photosensitive resin.

4. The microstructure manufacturing method according to claim 1, further comprising exposing the substrate surface by removing the entire first plated layer, and wherein the second plated layer is formed on part of the substrate surface exposed by removing the entire first plated layer.

5. The microstructure manufacturing method according to claim 1, wherein the second plated layer is formed on the first plated layer remained on the substrate surface.

6. The microstructure manufacturing method according to claim 1, wherein the substrate surface consists essentially of gold.

7. The microstructure manufacturing method according to claim 1, wherein the first plated layer consists essentially of nickel, copper, iron, tin or an alloy of them.

8. The microstructure manufacturing method according to claim 1, wherein the second plated layer consists essentially of gold.

9. The microstructure manufacturing method according to claim 1, wherein the photosensitive resin is a thermosetting resin, and wherein the structure of the photosensitive resin is cured by heating.

10. The microstructure manufacturing method according to claim 1, wherein the layer of the photosensitive resin is exposed to synchrotron radiation light.

11. The microstructure manufacturing method according to claim 1, wherein the microstructure is an X-ray absorption grating.

* * * * *